US011083671B2

(12) United States Patent
Kim et al.

(10) Patent No.: US 11,083,671 B2
(45) Date of Patent: Aug. 10, 2021

(54) PREPARATION FOR ATTACHING TO TEETH OR SURROUNDING PART OF TEETH

(71) Applicant: LG Household & Health Care Ltd., Seoul (KR)

(72) Inventors: Ji-Young Kim, Daejeon (KR); Jae-Hyun Ahn, Daejeon (KR); Jong-Hoon Kim, Daejeon (KR); In-Ho Lee, Daejeon (KR); Sang-Min Lee, Daejeon (KR)

(73) Assignee: LG Household & Health Care Ltd.

( * ) Notice: Subject to any disclaimer, the term of this patent is extended or adjusted under 35 U.S.C. 154(b) by 0 days.

(21) Appl. No.: 15/778,127

(22) PCT Filed: Nov. 10, 2016

(86) PCT No.: PCT/KR2016/012934
§ 371 (c)(1),
(2) Date: May 22, 2018

(87) PCT Pub. No.: WO2017/090921
PCT Pub. Date: Jun. 1, 2017

(65) Prior Publication Data
US 2018/0344582 A1 Dec. 6, 2018

(30) Foreign Application Priority Data
Nov. 24, 2015 (KR) .................. 10-2015-0164928
Dec. 3, 2015 (KR) .................. 10-2015-0171541

(51) Int. Cl.
*A61K 8/02* (2006.01)
*A61K 8/25* (2006.01)
*A61Q 11/00* (2006.01)
*A61K 8/69* (2006.01)
*A61K 8/19* (2006.01)
*A61K 8/81* (2006.01)
*A61K 9/06* (2006.01)
*A61K 8/73* (2006.01)
*A61K 47/02* (2006.01)
*A61K 47/36* (2006.01)
*A61K 47/12* (2006.01)
*A61K 9/00* (2006.01)
*A61K 9/70* (2006.01)

(52) U.S. Cl.
CPC .................. *A61K 8/02* (2013.01); *A61K 8/19* (2013.01); *A61K 8/25* (2013.01); *A61K 8/69* (2013.01); *A61K 8/731* (2013.01); *A61K 8/733* (2013.01); *A61K 8/81* (2013.01); *A61K 8/8129* (2013.01); *A61K 8/8164* (2013.01); *A61K 9/0063* (2013.01); *A61K 9/06* (2013.01); *A61K 9/70* (2013.01); *A61K 47/02* (2013.01); *A61K 47/12* (2013.01); *A61K 47/36* (2013.01); *A61Q 11/00* (2013.01); *A61K 8/736* (2013.01); *A61K 2800/882* (2013.01)

(58) Field of Classification Search
CPC . A61K 47/02; A61K 8/02; A61K 8/69; A61K 8/733; A61K 8/731; A61K 47/36; A61K 8/8164; A61K 8/19; A61K 8/25; A61K 8/81; A61K 8/8129; A61K 47/12; A61K 9/70; A61K 9/0063; A61K 9/06; A61K 6/30; A61K 2800/882; A61K 8/736; A61Q 11/00; A61P 1/02; C08L 33/08
See application file for complete search history.

(56) References Cited

U.S. PATENT DOCUMENTS

| 3,964,164 A | 6/1976 | Hesselgren |
| 5,122,061 A | 6/1992 | Wakumoto et al. |
| 5,989,569 A | 11/1999 | Dirksing et al. |
| 2002/0197214 A1 | 12/2002 | Bublewitz et al. |
| 2004/0086468 A1 | 5/2004 | Prosise et al. |
| 2006/0165607 A1* | 7/2006 | Tanaka ............... A61K 8/0208 424/47 |
| 2009/0286886 A1 | 11/2009 | Fisher et al. |

(Continued)

FOREIGN PATENT DOCUMENTS

| EP | 1566160 A2 | 8/2005 |
| EP | 3403644 A2 | 11/2018 |
| JP | 2006504783 A | 2/2006 |

(Continued)

OTHER PUBLICATIONS

Extended European Search Report including Written Opinion for Application No. EP168688182, dated Jun. 13, 2019, pp. 1-7.

(Continued)

Primary Examiner — Lezah Roberts
(74) Attorney, Agent, or Firm — Lerner, David, Littenberg, Krumholz & Mentlik, LLP

(57) ABSTRACT

The present invention provides a preparation for attaching to teeth or tooth peripheries, which comprises a malleable oral composition and an active ingredient for intra-oral delivery. Further, the present invention provides a preparation for attaching to teeth or tooth peripheries, which comprises an oral composition in a hardening ointment-phase and an active ingredient for intra-oral delivery. The preparation of the present invention may give high adhesive force to the desired site in spite of gaps between teeth or curves of teeth. The preparation of the present invention having high adhesive force increases the time of adhesion to a target site in the oral cavity, and thus may be advantageous in achieving an intended effect.

20 Claims, 4 Drawing Sheets

(56) References Cited

U.S. PATENT DOCUMENTS

2014/0212478 A1* 7/2014 Woo .................. A61K 31/05
                                                        424/450
2018/0344582 A1    12/2018 Kim et al.

FOREIGN PATENT DOCUMENTS

| KR | 1019880011259 A | 10/1988 |
| KR | 1020030005232 A | 1/2003 |
| KR | 102006021967 A | 3/2006 |
| KR | 1020060089892 A | 8/2006 |
| KR | 100623859 B1 | 9/2006 |
| KR | 20080004649 A | 1/2008 |
| KR | 102150057746 A | 5/2015 |
| KR | 1020150111646 A | 10/2015 |
| KR | 20170060460 A | 6/2017 |
| WO | 2001070178 A2 | 9/2001 |
| WO | 03037276 A1 | 5/2003 |
| WO | WO03/070218 * | 8/2003 |
| WO | 2007066837 A1 | 6/2007 |
| WO | 2010068359 A1 | 6/2010 |

OTHER PUBLICATIONS

International Search Report for PCT/KR2016/012934 dated Feb. 22, 2017.

* cited by examiner (a)

(b)

PREPARATION FOR ATTACHING TO TEETH OR SURROUNDING PART OF TEETH

CROSS-REFERENCE TO RELATED APPLICATIONS

This application is a national phase entry under 35 U.S.C. § 371 of International Application No. PCT/KR2016/012934, filed Nov. 10, 2016, which claims priority to Korean Patent Application No. 10-2015-0164928, filed Nov. 24, 2015, and Korean Patent Application No. 10-2015-0171541, filed Dec. 3, 2015, the disclosures of which are incorporated herein by reference.

TECHNICAL FIELD

The present invention relates to a preparation for delivering a drug into the oral cavity, and more specifically, it relates to a novel form of an oral preparation, which can effectively deliver an active ingredient to the desired site in the oral cavity.

BACKGROUND OF THE INVENTION

In order to deliver an oral active ingredient into the oral cavity, the contact time with an active ingredient and the delivery amount play an important role.

Paste formulations such as toothpaste have a disadvantage that it is difficult to provide sufficient contact time at the target site due to insufficient viscosity and high solubility, and mouth trays intended for intraoral drug delivery have a disadvantage that they have a strong sense of foreign body and difficult to deliver a drug locally due to their shape characteristics. Patch type or strip type is thin, so it is difficult to deliver sufficient amount of an active ingredient, and flexibility is low, so there is a disadvantage that it is difficult to be adhered to gaps between teeth, boundary area between gums and teeth, and the like.

In order to solve the adhesion problem to the gaps between teeth, boundary area between gums and teeth and the like, Korean Patent No. 10-0623859 developed a delivery system for a tooth whitening component using in situ gelling, but there was a disadvantage that it is necessary to use a separate backing layer because it is highly flowable when applied to the tooth surface. Further, WO 2003/037276 discloses a preparation to be sprayed in the oral cavity due to its low initial viscosity, but there was a problem that the difference between the normal storage temperature (especially in summer) and the temperature in the oral cavity is small and it is difficult to remove it because the phase transition does not occur rapidly unless it is applied very thin.

U.S. Pat. No. 5,989,569 discloses about applying a drug to the surface of a strip and delivering the drug by pressure, but there were problems that the active ingredient is temporarily released because the drug is applied on the surface of the strip and adhered to teeth as it is, and it may cause strong stimulus in the gums around the teeth. Further, there was a disadvantage that physical properties, in particular, flexibility, of the drug to be applied are different from those of the strip, and therefore, adhesion to gaps between teeth is difficult.

The inventors of the present invention have studied for a long time to develop a novel form of a preparation, which can effectively deliver a drug into the oral cavity with convenience of use, thereby completing the present invention.

SUMMARY OF THE INVENTION

In order to solve the above problems, the present invention provides a preparation for delivering an active ingredient whose physical properties are changed before attachment to teeth and after a period of time after the attachment.

Further, the present invention provides a preparation in a form that can be freely changed before use, and can be adhered well to gaps between teeth or a boundary area between gums and teeth.

Further, the present invention provides a novel form of an oral preparation having excellent feeling of use, which can be conveniently used without any feeling of being stained or sticky in the hands when attached to teeth or tooth peripheries.

These and other objects and advantages of the present invention may be understood from the following detailed description and will become more fully apparent from the exemplary embodiments of the present invention. Also, it will be easily understood that the objects and advantages of the present invention may be realized by the means shown in the appended claims and combinations thereof.

Definition

The term 'tooth peripheries' used herein is generally a concept involving a region represented by gums, and may be used to mean including all of the mucosal regions around teeth. The tooth peripheries can be used to mean covering the region where an active ingredient for intra-oral delivery can be delivered together with the teeth when the preparation is applied to the teeth in the structure of the preparation. Herein, 'teeth or tooth peripheries' is used together with 'teeth', and it may be understood herein to include both the teeth and the tooth peripheries even if it is described only as 'teeth'.

The term 'oral composition in a hardening ointment-phase' used herein means an oral composition that does not have a certain shape before adhered to teeth, has an ointment phase of free-shape transformation, gradually loses its fluidity, and its shape is fixed. Namely, it means an ointment-type oral composition, which has a characteristic that the preparation of the present invention is ointment type when the preparation is applied to teeth or tooth peripheries, after application, its viscosity increases up to the point of adhesion, and it hardens at the point when it is removed from teeth after adhesion.

The 'hardening ointment-phase' preparation may mean a preparation that is a semi-solid-type ointment such as dough or clay after application, but is molded with external force such as heat or pressure over time, gradually loses its moldability and hardens, and finally permanently transformed.

The term 'hardening' used herein may include not only hardening by the formation of a network structure such as an ionic crosslinked structure like an egg-box model but also a decrease in fluidity accompanied by a progress of polymerization reaction by light or a catalyst, and may mean a state of hardly hardening due to various factors such as degree of absorption of water and degree of exposure to air, and no further shape transformation.

The term 'malleability' used herein may mean that the preparation of the present invention has shape transformability or can have moldability by external pressure. It also mean that the preparation is sufficiently flexible and it is possible to transform to such a degree that when the preparation is adhered in the mouth, it can be completely adhered to gaps between teeth or the fine portion between teeth and gums.

Herein, not only the case that the preparation is stretched to the left and right but also the case that when it is placed on a flat surface and pressed with a certain force, the preparation is transformed by stretching in all directions can be included in the range of malleability. Further, any form causing change in appearance can be included in the range of malleability. With malleability, an object can be compressed or the area can be widened in a certain hardness range.

The term 'hardness' used herein may mean the amount of force required to compress the preparation. Hardness of the preparation of the present invention is measured at compression test mode of Stable Micro System TA XT Plus. After filling 20 g of the preparation into a 50 mL beaker, a 20 mm diameter aluminum probe for hardness measurement is set, and then hardness is measured with test speed of 1.5 mm/s, distance as target mode and distance of 10 mm. Hardness is understood as the peak value of the first cycle calculated. The unit can be expressed as g (g force).

The term 'compressibility' used herein may mean the force applied until just before the preparation is broken, cut or destroyed while it is compressed. Compressibility of the preparation of the present invention is measured at compression test mode of Stable Micro System TA XT Plus. After filling 20 g of the preparation into a 50 mL beaker, a 20 mm diameter aluminum probe for compressibility measurement is set, and then compressibility is measured with test speed of 1.5 mm/s, distance as target mode and distance of 10 mm. Compressibility is understood as the area value of the first cycle calculated. The unit can be expressed as gs (g force*sec).

The term 'compressibility' used herein may mean a characteristic that when compressing the preparation, it can expand without breaking or cutting while its volume is reduced.

The term 'elongation percentage' used herein means the degree to which the preparation can be stretched in all directions when load is applied, such as when a preparation is compressed between rollers. The term 'elongation percentage' used herein can be understood to mean "plane strain" unless otherwise specified. Good elongation percentage can be understood as having malleability.

Meaning of the term 'applied to teeth' used herein may include from immediately after application of the preparation to teeth to before the preparation adhered to teeth after a user applies pressure to the preparation. In the case of two-formulation type, the term 'after applying the preparation' in the present invention may mean after applying the mixture of the first formulation and the second formulation to teeth.

The term 'when adhering the preparation to teeth' in the present invention means the time of adhering the preparation to curves of teeth, gaps between teeth, or between teeth or gums by applying pressure after a certain period of time after application of the preparation to teeth, and preferably, the adhesion may be understood to be about 10 min or less, preferably about 5 min or less, more preferably about 1 to 3 min or less after applying the preparation of the present invention to teeth.

The term 'time of removal of the preparation' in the present invention may mean the time that the drug is released from the oral cavity after it is adhered to teeth or a surrounding tissue of teeth and then the preparation is removed therefrom. Depending on the purpose and use of the preparation, and the release amount of the drug, but it may be removed after 2 hr from attachment, but it may be removed within 30 min, more preferably within 10 min after adhered to teeth in view of convenience of use. Hardness of the preparation at the time of removal may be equal to the time at which the preparation is applied to teeth and the time at which the preparation is adhered to teeth, and hardness of the preparation at the time of removal may be increased.

The term 'preparation' used herein means to a product made by processing the active ingredient to ensure its therapeutic effect without affecting effectiveness of the active ingredient.

DETAILED DESCRIPTION OF THE INVENTION

The present invention provides a preparation for attaching to teeth or tooth peripheries, which comprises an oral composition in a hardening ointment-phase, and an active ingredient for intra-oral delivery. The present inventors have studied on a drug delivery system capable of delivering an active ingredient into the oral cavity, thereby suggesting a novel form of a drug delivery system and a novel method for delivering the active ingredient into the oral cavity using such a system.

The present inventors have studied for a long time on a novel drug delivery system capable of effectively delivering an active ingredient to specific sites in the oral cavity (for example, sites requiring tooth whitening, sites of oral inflammation, sites of periodontal disease, etc.). As a result, a novel form of an oral preparation, which can be conveniently applied to teeth or a mucosal region in the oral cavity, and can be adhered well to a curvy region and gaps between teeth so as to increase the drug reach rate at the desired site, has been developed.

One embodiment of the present invention provides a preparation for attaching to teeth or tooth peripheries, wherein an oral composition in a hardening ointment-phase and an active ingredient for intra-oral delivery are mixed. For example, the active ingredient can be homogeneously dispersed in the oral composition, and the case that the ingredient is inhomogeneously dispersed is also included in the mixing of the present invention.

According to one embodiment of the present invention, preparation of the present invention may substantially lose moldability at the time of the final removal, and preferably, at the time of the final removal, viscosity may be 5,000 cps or higher and moldability may be lost. The preparation may have viscosity of 5000 cPs or higher, preferably 10,000 cPs or higher, more preferably 200,000 cPs or higher, which is measured by using Brookfield viscometer equipped with No. 6, 7 spindles at a temperature of 20° C. (room temperature), 5 to 20 rpm, at the time of removal of the preparation after the preparation is applied to teeth or tooth peripheries and then the drug is released. Viscosity at the time of the final removal of the preparation may vary depending on the type and amount of a phase transition material, a phase transition auxiliary material, a material for helping attachment of the phase transition material and the like, contained in the preparation, and preferably, viscosity measured at the time of removal may be 5,000 cPs or higher and 104,000,000 cPs or less.

According to one embodiment of the present invention, the viscosity of the preparation attached to teeth, measured at the time of removal, may be increased two folds or more, preferably three folds or more, more preferably five folds or more, compared to the viscosity measured at the time of application of the preparation to teeth or tooth peripheries.

According to another embodiment of the present invention, the viscosity of the preparation of the present invention, measured at the time of removal, may be 5,000 cPs or higher, and may have a value two folds or more than the viscosity measured at the time of application to teeth.

The oral composition in a hardening ointment-phase contained in the preparation of the present invention may comprise a phase transition material, a phase transition auxiliary material, an attachment-enhancing material of the phase transition composition, and a material for helping drug release.

The phase transition material is a substance that causes hardening of the oral composition in a hardening ointment-phase. It may be carrageenan, pectin, xyloglucan, gellan gum, ammonium alginate, magnesium alginate, potassium alginate, sodium alginate, lithium alginate, chitosan, polylactic acid (poly(D,L-lactic acid)), polylactide-co-glycolide (poly(DL-lactide-co-glycolide)), poly-caprolactone, polyacrylic acid (carbopol), polyvinylacetal diethyl aminoacetate (AEA), hydroxypropylmethyl cellulose, poly(methacrylic acid)-poly(ethylene glycol), poly(D,L-lactide)-block-poly(ethylene glycol)-block-poly(D,L-lactide), PEG-oligoglycolyl-acrylate, poly(N-isopropyl acrylamide), sucrose acetate isobutyrate, polyvinyl alcohol, glyceryl monooleate, glyceryl monolinoleate, glyceryl monoarachidonate, glyceryl monostearate and the like alone or a combination of two or more thereof. Any material that can be used as a phase transition material in the art can be used and is not limited to the above examples.

The hardening ointment-phase composition may comprise the attachment-enhancing material of the phase transition composition, that is adhesive to teeth or has adhesiveness retention force; and that is well compatible with the phase transition material. For example, the material may be precipitated silica for thickening, colloidal silicone dioxide, polyvinyl pyrrolidone, poly methyl vinyl ether and maleic acid copolymers (gantrez), shellac, rosin, poloxamer, hyaluronic acid, acrylate copolymer (Eudragit L-100, L-100, 55), hydroxypropyl methyl cellulose (HPMC), hydroxypropyl cellulose (HPC), polyacrylic acid, polyethylene glycol, ethyl cellulose or a mixture thereof, but not limited thereto. Preferably, it may be hydroxypropyl methyl cellulose (HPMC) or ethyl cellulose or a mixture thereof. Such polymer can be used by dissolving thereof in water or a solvent (for example, ethanol), but crosslinked polymers also can be used. For example, the polymer may be crosslinked polyacrylic acid, or crosslinked polyvinyl pyrrolidone, and such crosslinked polymer can be used alone or in combination with a non-crosslinked polymer. In the case of a polymer obtained by cross-linking polymers having excellent adhesive force to teeth or gums, it is advantageous to improve adhesion of the composition as well as to improve the residuality because it is not dissolved in water or ethanol while exhibiting adhesive force after absorbing water.

The phase transition auxiliary material is a substance that can induce phase transition, control phase transition rate and adjust a degree of phase transition, and a calcium ion can be used. It is preferable that the calcium ion is water-soluble, but a calcium ion, which is insoluble in neutral or alkaline condition but can easily be converted into water-soluble in an acidic condition, also can be used. For example, the phase transition auxiliary material may be at least one selected from: a calcium ion source of calcium carbonate, calcium phosphate dibasic ($CaHPO_4$), barium carbonate, zinc carbonate, calcium chloride, calcium lactate, calcium citrate, calcium aspartate, calcium saccharate, calcium oxovalerate, calcium gluconate, calcium lactobionate and calcium lactogluconate; a chelating agent such as barium carbonate, zinc carbonate, sodium bicarbonate, sodium carbonate, tetraborate, tripolyphosphate, ethylenediamine tetraacetic acid, tetrasodium pyrophosphate, sodium acid pyrophosphate, Sporix (acidic sodium metaphosphate) and the like; acetic acid, malic acid, lactic acid, gluconic acid, ascorbic acid or a mixture thereof, or a salt thereof; and NaOH, KOH or a mixture thereof.

The phase transition material, the phase transition auxiliary material and the attachment-enhancing material of the phase transition material contained in the hardening ointment-phase composition are exemplarily listed, but not necessarily limited the above examples. According to another embodiment of the present invention, depending on the mechanism, the phase transition material, the phase transition auxiliary material and the attachment-enhancing material can be used indiscriminately. For example, if the phase transition material is polyvinyl alcohol, the phase transition auxiliary material may be tetraborate, and the material for enhancing adhesive force may be alginate or colloidal silica. In another embodiment, if the phase transition material is alginate, the phase transition auxiliary material may be calcium, and the material for enhancing adhesive force may be methyl vinyl ether and maleic acid copolymer (gantrez).

The material for helping drug release may be any material that can form a channel, a porous structure or bubble (foam) in the formulation. For example, in the case that the preparation is consisting of two formulations of the first formulation and the second formulation, one formulation contains an acid and the other contains a base, so that bubbles are formed in the formulation when the two formulations meet to form a hardening ointment-phase. Namely, the first formulation contains acetic, lactic, malic, gluconic, ascorbic acids and the like or a water-soluble salt thereof, e.g., sodium citrate, and the second formulation contains any base selected from the group consisting of sodium hydroxide (NaOH), potassium hydroxide (KOH), sodium bicarbonate (baking soda) and sodium carbonate. Preferably, the acid may be acetic acid, and the base may be sodium carbonate, and more preferably, those may be sodium citrate and sodium bicarbonate, which are an acid and a base mainly used in a toothpaste.

The active ingredient may include, for example, ingredients that can improve oral symptoms, and for example, it may be an ingredient for tooth whitening, an ingredient for preventing cavity containing a fluoride ion source, an ingredient for inhibiting tartar formation, an anti-inflammatory ingredient, an anti-bacterial ingredient, other vitamins, mineral ingredients and the like. Further, it may also include ingredients for improving sensitive teeth and for relieving its symptoms, and the like. More specifically, for example, it may include: at least one fluoride ion source selected from the group consisting of sodium fluoride, stannous fluoride, indium fluoride, amine fluoride and sodium monofluorophosphate; a reminerlaization agent containing hydroxyapatite; and an ingredient for tooth whitening selected from hydrogen peroxide, carbamide peroxide, calcium peroxide, perborate, percarbonate, peroxyacid, persulfate, calcium chloride, barium chloride, magnesium chloride, lithium chloride, sodium chloride or a mixture thereof. For enhancing whitening effect, a condensed phosphate can be used together with peroxides. The condensed phosphate, which can be used, may be at least one of tetrasodium pyrophosphate (TSPP), sodium acid pyrophosphate (SAPP), sodium tripolyphosphate (STP), sodium potassium pyrophosphate, tetrapotassium pyrophosphate, acidic sodium metaphosphate and acidic sodium polyphosphate, and it may be used together with peroxides. Such condensed phosphate also can be used for removing tartar or inhibiting tartar formation. Further, it can also contribute to the improvement of whitening effect by removing the metal which affects the stain formation of teeth as a chelating agent. The active ingredient may include an anti-bacterial agent including triclosan, chlorhexidine, alexidine, hexetidine, sanguinarine, benzalkonium chloride, salicylanilide, domiphen bromide, cetylpyridinium chloride (CPC), tetradecylpyridinium chloride (TPC) or a mixture thereof; an anti-inflammatory agent including aspirin, ketorolac, flurbiprofen, piroxicam, meclofenamic acid or a mixture thereof; thiamine, riboflavin, nicotinic acid, pantothenic acid, pyridoxine, biotin, folic acid, vitamin B12, lipoic acid, ascorbic acid, vitamin A, vitamin D, vitamin E, vitamin K or a mixture thereof; or a mixture thereof, but not limited thereto. Further, the drug effective for preventing and improving periodontal diseases may be titrated extract of *Zea Mays* L. unsaponifiable fraction, Magnoliae Cortex, Myrrha, Rhatany, Chamomile, policresulen, titrated extract of Centella Asiatica, nutmeg extract, dexpanthenol, β-sitosterol, acetyl salicylic acid and the like alone, or a mixture thereof of a certain mixing ratio. The ingredient for improving and relieving sensitive teeth symptoms may be zinc chloride, potassium phosphate, potassium diphosphate, calcium chloride, oxalic acid, potassium oxalate, ferric oxalate, vitamin E and the like alone, or a combination of two or more thereof.

According to one embodiment of the present invention, the preparation may be one-formulation type, or two-formulation type consisting of the first formulation and the second formulation, and three or more formulations may be mixed as required.

The first formulation and the second formulation of the two-formulation type preparation are mixed and applied to teeth or tooth peripheries, and in order to apply the preparation to teeth or tooth peripheries, the viscosity of the preparation measured after mixing the first formulation and the second formulation may be increased, compared to before mixing. After mixing, it may have moldability like dough.

The two-formulation type preparation may contain the active ingredient in the first formulation, the second formulation or both of the first formulation and the second formulation.

The two-formulation type preparation may selectively contain the phase transition material, the phase transition auxiliary material and the attachment-enhancing material in the first formulation, the second formulation or both of the first formulation and the second formulation.

For example, the two-formulation type preparation may contain magnesium alginate as a phase transition material in the first formulation. The two-formulation type preparation may contain calcium chloride as a material for helping hardening of the phase transition material, and hydroxypropyl cellulose as a material for helping attachment to teeth or tooth peripheries in the second formulation. In this case, the active ingredient may be appropriately contained in consideration of compatibility of the polymers contained in the first formulation and the second formulation, characteristics thereof and the like.

The preparation of the present invention may substantially lose moldability at the time of removal after attachment to teeth. Preferably, the time of removal may mean at 5 min to 3 hr, preferably 8 min to 90 min after application to teeth or tooth peripheries. For example, it may be removed after 10 min, 30 min or 1 hr from attachment.

In another embodiment, the time of removal after attachment to teeth may be, for example, the time at which the amount of the active ingredient contained in the preparation becomes 30 wt % or less, based on the total loaded weight of the drug at the beginning.

The substantially losing moldability means a hardening state in which the preparation loses physical properties such as dough and its shape transformation is not possible at the time of removal of the preparation after application. In one embodiment of the present invention, water-solubility of the preparation, measured at 32° C., 1 atm at a state of substantially losing moldability, may be 20 wt % or less, preferably 15 wt % or less, more preferably 10 wt % or less, and the most preferably 1 wt % to 10 wt %.

The preparation may further comprise a backing layer as required when it is attached to teeth or tooth peripheries. The backing layer may include a water-insoluble polymer, generally used in an oral film, and for example, polyethylene (PE), polypropylene (PP), ethylene vinyl acetate (EVA), cellulose acetate phthalate, shellac, polyvinyl acetate, ethyl cellulose, polymethyl methacrylate, methacryloylethyl betain/methacrylate copolymer (Yukaformer; Manufacturer: Mitsubishi), methacrylic acid copolymer (Eudragit L 100, Eudragit L 12, 5, Eudragit L 100-55, Eudragit L 30D-55), aminoalkyl methacrylate copolymer (Eudragit E 100, Eudragit E 12, 5, Eudragit RL 100, Eudragit RL 30D) and the like may be used.

The present invention provides a preparation for attaching to teeth or teeth and gums around teeth, which comprises a malleable oral composition, and an active ingredient for intra-oral delivery. The present inventors have studied on a drug delivery system capable of delivering an active ingredient into the oral cavity, thereby suggesting a novel form of a drug delivery system and a novel method for delivering the active ingredient into the oral cavity using such a system.

The present inventors have studied for a long time on a novel drug delivery system capable of effectively delivering an active ingredient to specific sites in the oral cavity (for example, sites requiring tooth whitening, sites of oral inflammation, sites of periodontal disease, etc.). As a result, a novel form of an oral preparation, which can conveniently be applied to teeth or a mucosal region in the oral cavity, and can be adhered well to a curvy region and gaps between teeth so as to increase the drug reach rate at the desired site, has been developed.

One embodiment of the present invention provides a preparation for attaching to teeth or tooth peripheries, wherein a malleable oral composition and an active ingredient for intra-oral delivery are mixed. For example, the active ingredient can be homogeneously dispersed in the oral composition, and the case that the ingredient is inhomogeneously dispersed is also included in the mixing of the present invention.

According to one embodiment of the present invention, the preparation of the present invention has semi-solid property at the same time, so that it can be adhered to curves or gaps.

The preparation of the present invention may have a form such as dough or clay, and it can be applied to teeth or tooth peripheries as the form of an ointment.

The preparation of the present invention may have the initial hardness in a range from 0.1 g to 20,000 g, preferably from 10 g to 12,000 g, measured at Compression mode of Texture Analyzer (TA), at the time of attachment. When the initial hardness is within the above range, the preparation can be easily adhered to gaps or curves of teeth.

The preparation may have the final hardness of 40,000 g or less, preferably 30,000 g or less, measured at Compression mode of Texture Analyzer (TA), at the time of removal.

The preparation having the final hardness within the above range can achieve the desired effect (for example, effect of improving sensitive teeth, tooth whitening effect, effect of preventing gingivitis and the like) by smoothly releasing the drug, and can have excellent shape fixing force.

In another embodiment of the present invention, the preparation may have the initial compressibility of 0.1 gs to 30,000 gs, preferably in a range from 10 gs to 20,000 gs, measured at Compression mode of Texture Analyzer (TA). When the compressibility is within the above range, the preparation can be easily adhered to gaps or curves of teeth.

The preparation may have the final compressibility of 50,000 gs or less, preferably 40,000 gs or less, measured at Compression mode of Texture Analyzer (TA).

The preparation having the final compressibility within the above range can achieve the desired effect (for example, effect of improving sensitive teeth, tooth whitening effect, effect of preventing gingivitis and the like) by smoothly releasing the drug, and can have excellent shape fixing force. Such shape fixing force can secure a sufficient contact time to the site where the drug is required to reach, and therefore, it can be more advantageous in achieving the desired effect.

The preparation according to one embodiment of the present invention may have malleability, which can increase length of the composition when pressing the preparation with a force of 0.5 kgf/cm$^2$ or more, preferably 1 kgf/cm$^2$ or more, at the beginning of attachment. Specifically, the preparation may have elongation percentage of 120% or more, preferably elongation percentage of 150% or more when pressing the preparation with a finger under conditions of standard relative humidity of 65% and 25° C., or when pressing with a pressure roller with a force of 0.5 kgf/cm$^2$ or more, preferably a force of 1 kgf/cm$^2$ or more. In another preferably embodiment, the preparation may have the elongation percentage of 120% or more and 500% or less.

Further, the malleability of the preparation of the present invention may be around 10% of the elongation percentage change from the time of application of the preparation to the teeth or tooth peripheries to the time of removal of the preparation. For example, in one embodiment of the present invention, the oral preparation of the preparation, wherein the first formulation containing PVA (polyvinyl alcohol) and the second formulation containing Borax are mixed, may have the same value of malleability and elongation percentage. Namely, the malleability which is measured at the time of application to the teeth surface, and the elongation percentage which is measured at the time of removal when the drug release has progressed by 60% or more after a certain period of time according to the method for measuring elongation percentage, i.e., a sample of a certain weight is made at size of 1 cm$^2$ and the sample is pressed with a pressure roller at a pressure of 2 kgf/cm$^2$, are the same as 150% and 150%, respectively.

The oral composition contained in the preparation of the present invention may comprise a phase transition material, a phase transition auxiliary material, an attachment-enhancing material of the phase transition composition, and a material for helping drug release.

The phase transition material is a substance which can cause cohesive property to the oral composition. It may be carrageenan, pectin, xyloglucan, gellan gum, ammonium alginate, magnesium alginate, potassium alginate, sodium alginate, lithium alginate, chitosan, poly-lactic acid (poly (D,L-lactic acid)), polylactide-co-glycolide (poly(DL-lactide-co-glycolide)), poly-caprolactone, polyacrylic acid (carbopol), polyvinylacetal diethyl aminoacetate (AEA), hydroxypropylmethyl cellulose, poly(methacrylic acid)-poly(ethylene glycol), poly(D,L-lactide)-block-poly(ethylene glycol)-block-poly(D,L-lactide), PEG-oligoglycolyl-acrylate, poly(N-isopropyl acrylamide), sucrose acetate isobutyrate, polyvinyl alcohol, polyvinyl acetate, glyceryl monooleate, glyceryl monolinoleate, glyceryl monoarachidonate, glyceryl monostearate and the like alone, or a combination of two or more thereof, and any material that can be used as a phase transition material in the art can be used, but not limited to the above examples.

The malleable oral composition may comprise the attachment-enhancing material of the phase transition composition, that is adhesive to teeth or has adhesiveness retention force; and that is well compatible with the phase transition material. For example, precipitated silica for thickening, colloidal silicone dioxide, polyvinyl pyrrolidone, poly methyl vinyl ether and maleic acid copolymers (gantrez), shellac, rosin, poloxamer, hyaluronic acid, acrylate copolymer (Eudragit L-100, L-100, 55), hydroxypropyl methyl cellulose (HPMC), hydroxypropyl cellulose (HPC), polyacrylic acid, polyethylene glycol, ethyl cellulose or a mixture thereof, but not limited thereto. Preferably, it may be hydroxypropyl methyl cellulose (HPMC) or ethyl cellulose or a mixture thereof. Such polymer can be used by dissolving thereof in water or a solvent (for example, ethanol), but crosslinked polymers also can be used. For example, the polymer may be crosslinked polyacrylic acid, or crosslinked polyvinyl pyrrolidone, and such crosslinked polymer can be used alone or in combination with a non-crosslinked polymer. In the case of a polymer obtained by cross-linking polymers having excellent adhesive force to teeth or gums, it is advantageous to improve adhesion of the composition as well as to improve the residuality because it is not dissolved in water or ethanol while exhibiting adhesive force after absorbing water.

The phase transition auxiliary material is a substance that can induce phase transition, control phase transition rate and adjust a degree of phase transition, and a calcium ion can be used. It is preferable that the calcium ion is water-soluble, but a calcium ion, which is insoluble in neutral or alkaline condition but can easily be converted into water-soluble in an acidic condition, also can be used. For example, the phase transition auxiliary material may be at least one selected from: a calcium ion source of calcium carbonate, calcium phosphate dibasic (CaHPO$_4$), barium carbonate, zinc carbonate, calcium chloride, calcium lactate, calcium citrate, calcium aspartate, calcium saccharate, calcium oxovalerate, calcium gluconate, calcium lactobionate and calcium lactogluconate; a chelating agent such as barium carbonate, zinc carbonate, sodium bicarbonate, sodium carbonate, tetraborate, tripolyphosphate, ethylenediamine tetraacetic acid, tetrasodium pyrophosphate, sodium acid pyrophosphate, Sporix (acidic sodium metaphosphate), trisodium trimetaphosphate and the like; acetic acid, malic acid, lactic acid, gluconic acid, ascorbic acid, boric acid or a mixture thereof, or a salt thereof; and NaOH, KOH or a mixture thereof.

The phase transition material, the phase transition auxiliary material and the attachment-enhancing material of the phase transition material contained in the composition are exemplarily listed, but not necessarily limited the above examples. According to another embodiment of the present invention, depending on the mechanism, the phase transition material, the phase transition auxiliary material and the attachment-enhancing material can be used indiscriminately. For example, if the phase transition material is polyvinyl alcohol, the phase transition auxiliary material may be tetraborate, and the material for enhancing adhesive force may be alginate or colloidal silica. In another embodiment, if the phase transition material is alginate, the phase transition auxiliary material may be calcium, and the material for enhancing adhesive force may be methyl vinyl ether and maleic acid copolymer (gantrez).

The material for helping drug release may be any material that can form a channel, a porous structure or bubble (foam) in the formulation. For example, in the case that the preparation is consisting of two formulations of the first formulation and the second formulation, one formulation contains an acid and the other contains a base, so that bubbles are formed in the formulation when the two formulations meet to form a viscous malleable composition. Namely, the first formulation contains acetic acid, lactic acid, malic acid, gluconic acid, ascorbic acid and the like or a water-soluble salt thereof, e.g., sodium citrate, and the second formulation contains at least one base selected from the group consisting of sodium hydroxide (NaOH), potassium hydroxide (KOH), sodium bicarbonate (baking soda) and sodium carbonate. Preferably, the acid may be acetic acid, and the base may be sodium carbonate, and more preferably, those may be sodium citrate and sodium bicarbonate, which are an acid and a base mainly used in a toothpaste.

The active ingredient may include, for example, ingredients that can improve oral symptoms, and for example, it may be an ingredient for tooth whitening, an ingredient for preventing cavity containing a fluoride ion source, an ingredient for inhibiting tartar formation, an anti-inflammatory ingredient, an anti-bacterial ingredient, other vitamins, mineral ingredients and the like. Further, it may also include ingredients for improving sensitive teeth and for relieving its symptoms, and the like. More specifically, for example, it may include: at least one fluoride ion source selected from the group consisting of sodium fluoride, stannous fluoride, indium fluoride, amine fluoride and sodium monofluorophosphate; a reminerlaization agent containing hydroxyapatite; and an ingredient for tooth whitening selected from hydrogen peroxide, carbamide peroxide, calcium peroxide, perborate, percarbonate, peroxyacid, persulfate, calcium chloride, barium chloride, magnesium chloride, lithium chloride, sodium chloride or a mixture thereof. For enhancing whitening effect, a condensed phosphate can be used together with peroxides. The condensed phosphate, which can be used, may be at least one of tetrasodium pyrophosphate (TSPP), sodium acid pyrophosphate (SAPP), sodium tripolyphosphate (STP), sodium potassium pyrophosphate, tetrapotassium pyrophosphate, acidic sodium metaphosphate and acidic sodium polyphosphate, and it may be used together with peroxides. Such condensed phosphate also can be used for removing tartar or inhibiting tartar formation. Further, it can also contribute to the improvement of whitening effect by removing the metal which affects the stain formation of teeth as a chelating agent. The active ingredient may include an anti-bacterial agent including triclosan, chlorhexidine, alexidine, hexetidine, sanguinarine, benzalkonium chloride, salicylanilide, domiphen bromide, cetylpyridinium chloride (CPC), tetradecylpyridinium chloride (TPC) or a mixture thereof; an anti-inflammatory agent including aspirin, ketorolac, flurbiprofen, piroxicam, meclofenamic acid or a mixture thereof; thiamine, riboflavin, nicotinic acid, pantothenic acid, pyridoxine, biotin, folic acid, vitamin B12, lipoic acid, ascorbic acid, vitamin A, vitamin D, vitamin E, vitamin K or a mixture thereof; or a mixture thereof, but not limited thereto. Further, the drug effective for preventing and improving periodontal diseases may be titrated extract of *Zea Mays* L. unsaponifiable fraction, Magnoliae Cortex, Myrrha, Rhatany, Chamomile, policresulen, titrated extract of Centella Asiatica, nutmeg extract, dexpanthenol, β-sitosterol, acetyl salicylic acid and the like alone, or a mixture thereof at a certain mixing ratio. The ingredient for improving and relieving sensitive teeth symptoms may be zinc chloride, potassium phosphate, potassium diphosphate, calcium chloride, oxalic acid, potassium oxalate, ferric oxalate, vitamin E and the like alone, or a combination of two or more thereof.

According to one embodiment of the present invention, the preparation may be one-formulation type, or two-formulation type consisting of the first formulation and the second formulation, and three or more formulations may be mixed as required.

The first formulation and the second formulation of the two-formulation type preparation are mixed and applied to teeth or tooth peripheries, and in order to apply the preparation to teeth or tooth peripheries, the viscosity of the preparation measured after mixing the first formulation and the second formulation may be increased, compared to before mixing, it may have moldability like dough after mixing, and may have malleability.

The two-formulation type preparation may contain the active ingredient in the first formulation, the second formulation or both of the first formulation and the second formulation.

The two-formulation type preparation may selectively contain the phase transition material, the phase transition auxiliary material and the attachment-enhancing material in the first formulation, the second formulation or both of the first formulation and the second formulation.

For example, the two-formulation type preparation may contain magnesium alginate as a phase transition material in the first formulation. The two-formulation type preparation may contain calcium chloride as a material for helping hardening of the phase transition material, and hydroxypropyl cellulose as a material for helping attachment to teeth or tooth peripheries in the second formulation. In this case, the active ingredient may be appropriately contained in consideration of compatibility of the polymers contained in the first formulation and the second formulation, characteristics thereof and the like.

Physical properties such as hardness, compressibility and the like of the preparation of the present invention may be maintained the same from right after attachment to just before removal, and depending on the purpose, the physical properties may be maintained the same until the sufficient amount of drug is released in the oral cavity, but at the time of removal, hardness may be somewhat increased to fix the shape. The time of removal of the preparation of the present invention may vary depending on ingredients contained in the preparation, but it may mean at 30 min after application to teeth or tooth peripheries.

In another embodiment, the time of removal after attachment to teeth may be, for example, the time at which drug release rate into the oral cavity becomes 60 wt % or more, preferably 65 wt % or more, more preferably 70 wt % or more, based on the amount of the drug contained in the preparation at the beginning.

The preparation may further comprise a backing layer as required when it is attached to teeth or tooth peripheries. The backing layer may include a water-insoluble polymer, generally used in an oral film, and for example, polyethylene (PE), polypropylene (PP), ethylene vinyl acetate (EVA), cellulose acetate phthalate, shellac, polyvinyl acetate, ethyl cellulose, polymethyl methacrylate, methacryloylethyl betain/methacrylate copolymer (Yukaformer; Manufacturer: Mitsubishi), methacrylic acid copolymer (Eudragit L 100, Eudragit L 12, 5, Eudragit L 100-55, Eudragit L 30D-55), aminoalkyl methacrylate copolymer (Eudragit E 100, Eudragit E 12, 5, Eudragit RL 100, Eudragit RL 30D) and the like may be used.

In one embodiment of the present invention, the preparation can be easily removed at the time of removal after drug release by tooth brushing, and the time of removal may be at the time after 30 min after attachment.

Advantageous Effects

The preparation of the present invention can give high adhesive force to the desired site despite gaps between teeth or curves of teeth.

The preparation is adhered well to gaps between teeth, thereby having excellent drug delivery efficiency. Further, it is possible to sufficiently secure the contact time between the drug delivery site and the preparation of the present invention because the preparation does not flow down or is not diluted with saliva after attachment, and therefore, it is advantageous to achieve the desired efficacy.

Further, the preparation can be used conveniently because it does not flow down when applied to teeth.

BRIEF DESCRIPTION OF THE DRAWINGS

Other objects and aspects of the present invention will become apparent from the following descriptions of the embodiments with reference to the accompanying drawings in which:

The accompanying drawings illustrate a preferred embodiment of the present invention and together with the foregoing disclosure, serve to provide further understanding of the technical spirit of the present invention, and thus, the present invention is not construed as being limited to the drawing.

Figure 1:
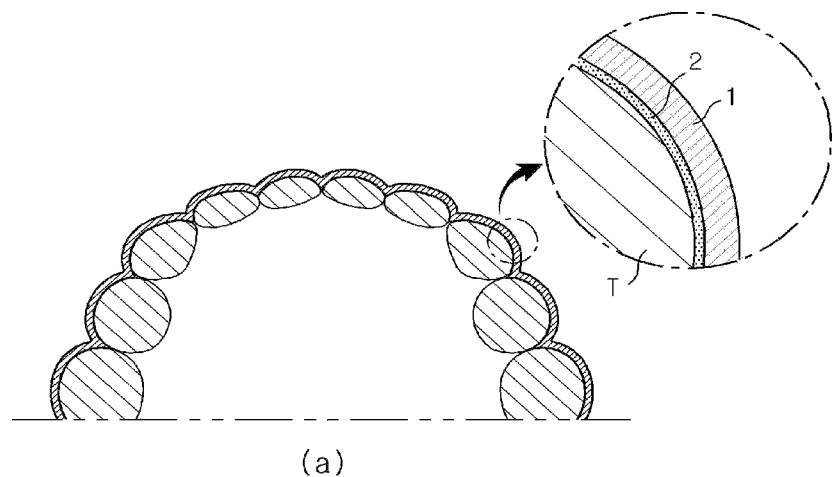
Figure 1:
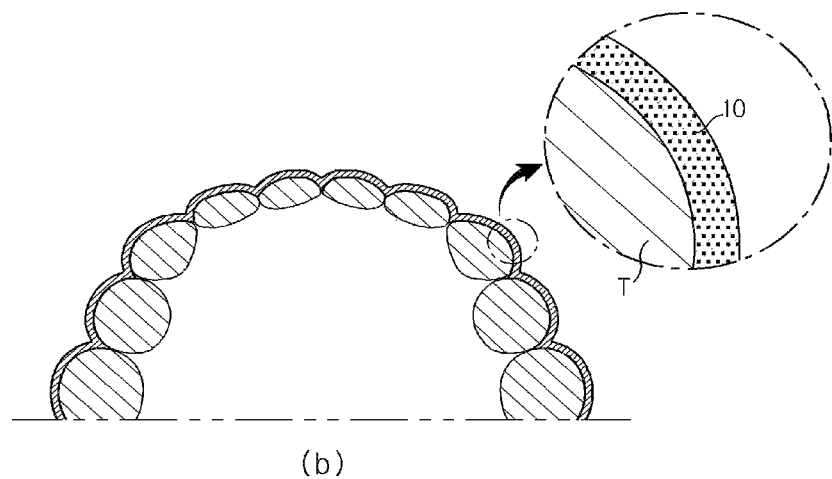

In the drawing, T refers to teeth, and 1 refers to the conventional strip for attaching to teeth. 2 refers to an active ingredient, and 10 refers to the oral preparation manufactured according to one embodiment of the present invention.

FIG. 1 is a drawing showing (a) the conventional strip for attaching to the oral cavity and (b) the preparation according to one embodiment of the present invention. Unlike the conventional strip wherein an active ingredient 2 and a strip 1 are in separate layers, the preparation according to one embodiment of the present invention can have the form that the drug is dispersed in the preparation.

Figure 2:
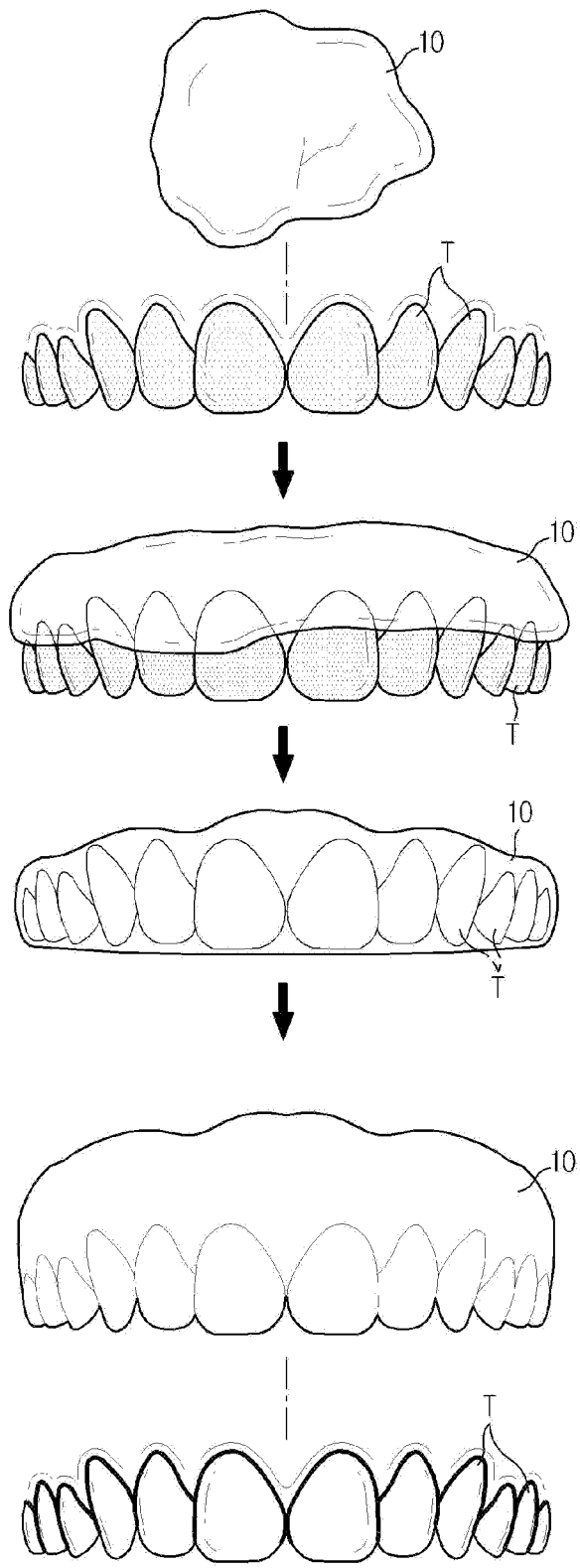

FIG. 2 is a drawing prefiguratively showing the process of attaching the preparation of the present invention 10 to teeth T and then removing the preparation from the teeth over time.

Figure 3:
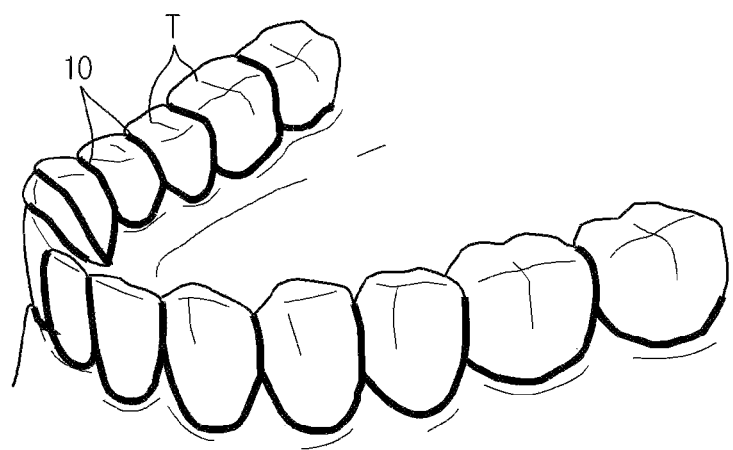

FIG. 3 is a drawing prefiguratively showing the process of hardening the preparation according to one embodiment of the present invention after applying and adhering the preparation to teeth. As can be seen from FIG. 3, the preparation of the present invention can reach gaps between teeth.

Figure 4:
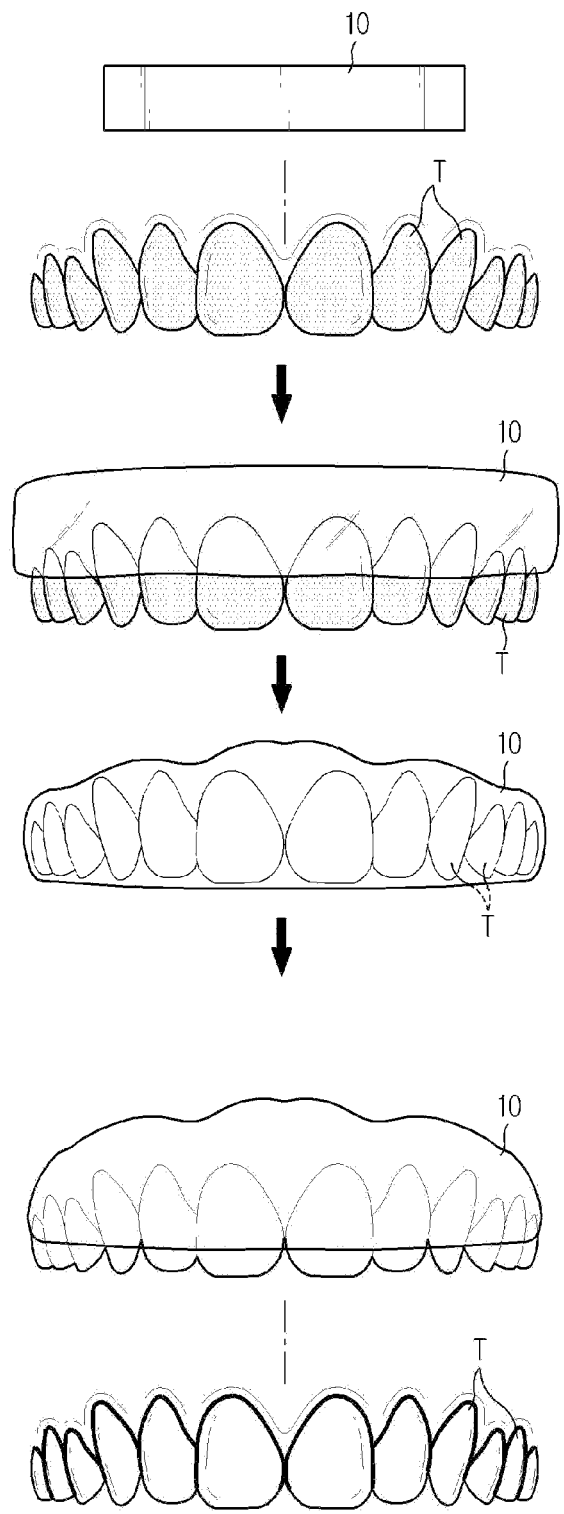

FIG. 4 is a drawing prefiguratively showing the process of attaching the preparation 10 to teeth T and then removing the preparation from the teeth over time according to another embodiment of the present invention.

EXAMPLES

Hereinafter, the present invention will be described in more detail through the following embodiments. However, the embodiments according to the present invention may be modified in many different forms, and the scope of the present invention shall not be construed as being limited to the embodiments described below. The embodiments of the present invention are provided for illustration to help a full understanding of the present invention. Unless stated otherwise, % used herein are understood to mean wt %.

Preparation and Test of Oral Composition in a Hardening Ointment-Phase

[Preparation of Oral Preparation]

Oral preparations of Examples and Comparative Examples having the following composition were prepared or purchased.

Preparations of Examples 1 to 3 were manufactured according to the following method. The powder preparation of Example was mixed by using a powder mixer, the gel of Example was prepared by mixing a polymer with a mechanical mixer at a constant rate without aggregation. Further, Example 3 was prepared by mixing with a mechanical mixer after adjusting temperature to 50° C.

TABLE 1

| | Example 1 (Film coating type with separate backing layer) | | Example 2 (Dual paint type with applicator (dual syringe + mixing tip)) | | Example 3 (Gel type, which is Phase transition type by saliva) |
| --- | --- | --- | --- | --- | --- |
| First formulation (powder) | | Alginate 12% Calcium Sulfate 15% Sodium Phosphate 2% Diatomite to 100% | First formulation (gel-like) | Alginate 3.8% Acetic Acid 2.5% Magnoliae Cortex 0.1% (active ingredient) Water to 100% | GMO 48.0% EC 8.0% Hydrogen Peroxide 6% (active ingredient) Ethanol 44.0% |
| Second formulation (liquid-like viscosity) Backing layer | | Gantrez 0.38% Zinc Chloride 0.18% (active ingredient) Water to 100% PE film | Second formulation (gel-like) | Alginate 3.8% Calcium Carbonate 2.0% Sodium Carbonate 1.9% Water to 100% | |

Comparative Examples 1 to 5 were prepared. Comparative Example 1 used P&G SensiStop (containing active ingredient of improving sensitive teeth) and Comparative Example 2 used Parodontax (containing active ingredient of improving gingivitis).

Comparative Example 3 used Alginate Gel prescription (alginate water-soluble gel prescription, tooth whitening), Comparative Example 4 used Poloxamer prescription as a Temperature Sensitive Polymer (tooth whitening) and Comparative Example 5 used dental impression material prescription (silicone dual-syringe prescription).

iii) Viscosity just before removal or upon completion of drug release (the time at which about 70% to 100% of drug is released): it means the viscosity when no further viscosity increase occurs.

For example, in the case of a prescription for tooth whitening and maintaining the whitening effect, which consists of the first formulation and the second formulation, and is attached for 30 min, ① Viscosity at the time of manufacture means each viscosity before mixing, ② Viscosity at the first application means the viscosity just before application to teeth (when consisting of the first formulation and the

TABLE 2

| Comparative Example 1 (P&G SensiStop ™) Formulation: Strip | Comparative Example 2 (Product name: Parodontax ™) Formulation: Toothpaste | Comparative Example 3 (Alginate Gel) Formulation: Gel | Comparative Example 4 (Poloxamer) Formulation: Liquid | Comparative Example 5 Dental impression material (Selection VPS Putty) Formulation: Reactive silicone gel (First formulation, Second formulation) |
|---|---|---|---|---|
| Water Glycerin Cellulose Gum Dipotassium Oxalate (active ingredient) Carbomer Sodium Hydroxide Sodium Benzoate Potassium Sorbate PE film | Myrrha tint Rhatany tint Chamomile tint | Alginate 1.5% Hydrogen Peroxide 6% Water to 100% | PluronicF127 20% Carbamide Peroxide 16% ($H_2O_2$ 5.6%) Water to 100% | Vinyl Polysiloxane Impression Material (First formulation, Second formulation) |

[Test for Comparing Viscosity, Solubility and Convenience of Use Before Attachment or at the Beginning of Attachment and Just Before Removal]

Test Method

1. Viscosity comparison test (Test method: Viscosity was measured by using Rotary Viscometer)

Evaluation device: Brookfield Viscometer, No. 6, or 7 spindle, 5 rpm to 20 rpm, 20° C. (room temperature)

Evaluation method: Viscosity of Comparative Example and Example was measured by using Brookfiled Viscometer.

As follows, i) viscosity at the first application, ii) viscosity in adhesion, iii) and viscosity just before removal were measured. But, in the case of the prescription consisting of the first formulation and the second formulation, each viscosity measured before mixing the first formulation and the second formulation was referred to as the viscosity at the time of manufacture, and in the case of consisting of only the first formulation, the viscosity at the time of manufacture was referred to the same as the viscosity before the first application.

i) Viscosity at the first application: in the case of consisting of the first formulation and the second formulation, it is the same as the viscosity right after mixing, and in the case of consisting of only the first formulation, it is the same as the viscosity at the time of manufacture.

ii) Viscosity in adhesion: in the case of consisting of the first formulation and the second formulation, the viscosity is increased from the moment of mixing, and the viscosity means the viscosity in the state where shape transformation can occur even at a small pressure. In this test, for example, in the case of a preparation whose total use time is 10 min, the preparation was adhered to the desired site at 5 min after application, and in the case of a preparation whose total use time is 30 min, the preparation was adhered to the desired site at 5 min to 10 min after application. The viscosity at this time was measured as the viscosity in adhesion.

second formulation, it means the viscosity right after mixing) ③ Viscosity in adhesion means the viscosity at 10 min after application to teeth, ④ Viscosity just before removal or upon completion of drug release means the viscosity at 30 min after application to teeth.

2. Drug release rate comparison test (Test method: after releasing test, the concentration of an active ingredient in a solution was quantified)

A) Manipulation 0.9% Sodium chloride solution 500 mL is poured in a test tube and a temperature of a test solution is maintained at 32±0.5° C. during drug release test. Example or Comparative Example as a sample is fixed on the upper side of a disk which can be used as a sinker without absorbing, interfering or reacting so that a target attachment surface faces outward. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per min (rpm) is set to 25. At the time of sampling, 100 mL of sample solution is collected at a fixed position (a position 1 cm away from the wall of the test tube, between the top of the paddle blade and the test liquid surface) 30 min after the start of the test.

Drug analysis method: Depending on the drug or the content, an appropriate analysis is selected. For example, peroxides are analyzed by titration, metal salts are analyzed by ICP analysis, and natural extracts are analyzed by HPLC.

3. Solubility comparison test: In the present invention, solubility is defined as shape retention force during artificial saliva (0.9% NaCl aqueous solution) release test. Recorded through comparative observation (Whether the shape is collapsed or maintained, or the same thickness and height are maintained or decreased in the USP drug release test was observed and recorded)

① Solubility at the time of manufacture: in the case of consisting of the first formulation and the second formulation, 1 g each was taken and loaded in the same manner as the drug release test, and then solubility was observed.

② In the case of consisting of the first formulation and the second formulation, solubility at the first application, in adhesion and just before removal was measured by loading the drug in the same manner as the drug release test, and observing shape transformation over time.

4. Convenience of use comparison test (Whether wet type or dry type): The characteristics of the formulation applied to the target in the oral cavity cause the inconvenience to use because the formulation is smeared to the hands while being applied. Further, those cause the inconvenience to use because the formulation is smeared to gums or hands while applying and standing for a certain time and is smeared to the hand during removal. Wet type is characterized in that it is smeared to the hands when touched, and dry type is characterized in that it is not smeared when touched by hands because it maintains its shape.

[Efficacy/Effect Comparison Test]

1. Clinical survey related to improvement of sensitive teeth for humans

1) Test subject and instructions: Example 1 group and Comparative Example 1 group were attached to the sensitive teeth area for 10 min once a day and then removed.

2) After 1 week use, the survey was conducted to 15 volunteers who felt sensitive teeth per each group using 3-point Likert scale.

3) Criteria 1 point: Compared to before use, the sensitive teeth symptoms were similar or worsened.

2 point: Compared to before use, the sensitive teeth symptoms were slightly relieved.

3 point: Compared to before use, the sensitive teeth symptoms were a lot relieved.

2. Clinical survey related to improvement of gingivitis symptoms-relief of gum pain for humans 1) Test subject and instructions: Example 2 group and Comparative Example 2 group were attached to the gum pain area for 10 min once a day and then removed.

2) After 1 week use, the survey was conducted to 15 volunteers who felt gum pain per each group using 3-point Likert scale.

3) Criteria 1 point: Compared to before use, the gum pain symptoms were similar or worsened.

2 point: Compared to before use, the gum pain symptoms were slightly relieved.

3 point: Compared to before use, the gum pain symptoms were a lot relieved.

3. Evaluation of whitening effect by in vitro tooth whitening evaluation method using artificial teeth (1) Preparation and Coloring of Hydroxyapatite (HAP) Tablet Sample Artificial teeth were made by using hydroxyapatite, a component that forms 96% or more of teeth. Namely, hydroxyapatite powder was tableted with IR press or tablet machine and then sintered at 1000° C. According to Stookey method, a process of impregnating a sample in TSB (trypticase soybroth) solution in which tea, coffee, iron and mucin protein were dissolved and drying thereof was repeated for 1 week to prepare a colored artificial sample. The colored sample was washed lightly with running water using a toothbrush to remove stains that could be easily dissolved or easily removed by water, and then dried. The initial L (lightness) value was measured with a chroma meter.

(2) In Vitro Tooth Whitening Evaluation Method Using Colored Artificial Teeth

After attaching Example 3, Comparative Example 3 and Comparative Example 4 to a colored artificial teeth, respectively, the artificial teeth was allowed to stand for 30 min under conditions of the oral cavity, i.e., 37° C., 98% humidity. The sample was washed with water after removing Example and Comparative Example and then dried. Then, L value was measured. The delta L value, which is the difference between the L values before and after attachment, was calculated.

[Test for Comparing Viscosity and Solubility Before Attachment or at the Beginning of Attachment and Just Before Removal]

1. Viscosity of Example and Comparative Example at each stage (At this time, viscosity at each stage may have an error range of about +/−50 cPs.)

TABLE 3

| | Example 1 | Example 2 | Example 3 | Comparative Example 3 | Comparative Example 4 | Comparative Example 5 |
|---|---|---|---|---|---|---|
| At the time of manufacture | Second formulation (5 cps) | First formulation (14,000 cps) Second formulation (14,000 cps) | 1,150 cps | 13,000 cps | 400 cps | First formulation (700,000 cps) Second formulation (700,000 cps) |
| First application | 30,000 cps | 20,000 cps | 1200 cps | 13,000 cps | 400 cps | 700,000 cps |
| In adhesion | 120,000 cps | 50,000 cps | 2500 cps* | 13,000 cps | 600 cps | >2,000,000 cps |
| Just before removal (Upon completion of drug release) | 180,000 cps | >50,000 cps | >5000 cps* | 13,000 cps | 600 cps | Not measurable |

As listed in Table 3, it was confirmed that after the first application of the preparation, the viscosity of the preparations of Examples of the present invention was increased until adhesion of the preparations.

2. Drug release rate of Example and Comparative Example at each stage

TABLE 4

| | Example 1 | Example 3 | Comparative Example 5 |
|---|---|---|---|
| After 10 min from attachment | 50% | 60% | 5% |
| After 30 min from attachment | >70% | >80% | <5% |

As can be seen from Table 4, when the total loaded amount of drug is referred as 100, it can be found that 70% or more of the drug was released at the time of removal of the preparation, which was 30 min after attachment. However, in the case of Comparative Example 5 corresponding to a dental impression material, it can be found that increase of the viscosity over time is the same as the preparation of the present invention showed, but drug release was not smooth.

3. Solubility/shape retention force of preparation of Example and Comparative Example at each stage

TABLE 5

|  | Example 1 | Example 2 | Comparative Example 3 | Comparative Example 4 | Comparative Example 5 |
|---|---|---|---|---|---|
| Solubility at the time of manufacture | Second formulation (Dissolved) | First formulation (Dissolved) Second formulation (Dissolved) | Dissolved | Dissolved | First formulation (Maintained shape 100%) Second formulation (Maintained shape 100%) |
| Solubility at first application | Maintained shape (100%) | Maintained shape (>90%) | Dissolved | Partly maintained shape (>50%) | Maintained shape (100%) |
| Preparation residue just before removal | Maintained shape (100%) | Maintained shape (>90%) | Dissolved | Partly maintained shape (<50%) | Maintained shape (100%) |

As can be seen from Table 5, it can be found that the preparations of the present invention have excellent shape retention force just before removal. Namely, from the above results, it can be found that the preparations of the present invention can be adhered to fit to gaps between teeth after application, and its shape can be maintained just before removal.

4. Comparison of convenience of use of Example and Comparative Example

TABLE 6

|  | Example 1 | Example 2 | Comparative Example 1 | Comparative Example 2 | Comparative Example 4 |
|---|---|---|---|---|---|
| Degree of smear at the time of manufacture | Second formulation (Smeared: Wet type) | First formulation (Smeared: Wet type) Second formulation (Smeared: Wet type) | Smeared (Wet type) | Smeared (Wet type) | Smeared (Wet type) |
| Degree of smear at first application | Almost not smeared (Like dry type) | Almost not smeared (Like dry type) | Smeared (Wet type) | Smeared (Wet type) | Smeared (Wet type) |
| Degree of smear just before removal | Not smeared | Not smeared | Smeared (Wet type) | Smeared (Wet type) | Smeared (Wet type) |

Table 6 shows the result of confirming convenience of use in the course of applying the preparations of the present invention. As can be seen from the above result, it was confirmed that the preparations of the present invention can be used conveniently and sanitarily because the drug was almost not smeared to the hands when applied and adhered to teeth, and there is no unnecessary loss of the drug. However, the preparations of Comparative Examples gave loss of the drug or inconvenience because the drug was smeared to the hands.

5. Comparison of efficacy of Example and Comparative Example

TABLE 7

|  | Example 1 | Comparative Example 1 | Example 2 | Comparative Example 2 |
|---|---|---|---|---|
| Survey score for sensitive teeth symptom | 2.7 | 1.5 |  |  |
| Survey score for gum pain |  |  | 2.4 | 1.4 |

As can be seen from Table 7, it was confirmed that Example 1 had better effect of relieving sensitive teeth, compared to Comparative Example 1, and it was confirmed that Example 2 had better effect of relieving gum pain symptoms, compared to Comparative Example 2.

These results suggest that the formulations of Examples of the present invention have excellent degree of adhesion to teeth and gaps between teeth, so that active ingredients are effectively delivered to the target site.

Further, because Comparative Examples 1 and 2 are toothpaste-type and the holding time of the drug delivered at the time of the first application (brushing) was not long, the active ingredient gradually disappeared over time. However, in the case of the preparation of Examples of the present invention providing the time for stable penetration of the active ingredient for a certain period of time, it was thought that loss rate of the active ingredient was low.

TABLE 8

|  | ΔL(Use once) | ΔL(Use twice) |
|---|---|---|
| Example 3 | 16.54 ± 2.19 | 31.49 ± 3.05 |
| Comparative Example 3 | 5.29 ± 1.54 | 9.89 ± 1.85 |
| Comparative Example 4 | 7.82 ± 3.19 | 13.26 ± 1.99 |

As can be seen from Table 8, Example 3 showed better tooth whitening effect, compared to Comparative Examples 3 and 4. It was confirmed that in the case of Comparative Examples 3 and 4, which are gel-type and liquid-type, respectively, the amount of the active ingredient delivered to teeth was smaller than the loaded amount, and the whitening effect was significantly low because the amount that flows down or disappears without being fixed after being applied to teeth was a lot.

Preparation and Test of Oral Preparation Having Malleability

Additional oral preparations, including Examples and Comparative Examples having the same composition as some of Examples 1 to 3 and Comparative Examples, were prepared and the following tests were conducted.

[Preparation of Oral Preparation]

TABLE 9

|  | Example 1 (Film coating type with separate backing layer) |  | Example 2 (Dual paint type with applicator (dual syringe ± mixing tip)) | Example 3 (Gel type, which is Phase transition type by saliva) | Example 4 (Compression band type, Example having form like plaster) |
|---|---|---|---|---|---|
| First formulation (powder) | Alginate 12% Calcium Sulfate 15% Sodium Phosphate 2% Diatomite to 100% | First formulation (gel-like) | Alginate 3.8% Acetic Acid 2.5% Magnoliae Cortex extract 0.1% (active ingredient) Water to 100% | First formulation: Gel-like Second formulation: GMO 48.0% EC 8.0% Hydrogen Peroxide 6% (active ingredient) Ethanol 44.0% | First formulation (Liquid): PVA 3% Magnoliae Cortex extract 0.1% Ethanol 1% Water to 100% |
| Second formulation (liquid-like viscosity) | Gantrez 0.38% Zinc Chloride 0.18% (active ingredient) Water to 100% | Second formulation (gel-like) | Alginate 3.8% Calcium Carbonate 2.0% Sodium Carbonate 1.9% Water to 100% |  | Second formulation (Liquid): Borax 4% |
| Backing layer | PE film |  |  |  |  |

Comparative Examples 1 to 3 and 5 were prepared as follows.

TABLE 10

|  | Comparative Example 1 (P&G SensiStop ™) Formulation: Strip | Comparative Example 2 (Product name: Parodontax ™) Formulation: Toothpaste | Comparative Example 3 (Alginate Gel) Formulation: Gel | Comparative Example 5 Dental impression material (Selection VPS Putty) Reactive silicone gel (Formulation: First formulation, Second formulation) |
|---|---|---|---|---|
|  | Water Glycerin Cellulose Gum Dipotassium Oxalate (active ingredient) Carbomer Sodium Hydroxide | Myrrha tint Rhatany tint Chamomile tint | Alginate 1.5% Hydrogen Peroxide 6% Water to 100% | Vinyl Polysiloxane Impression Material (First formulation, Second formulation) |

TABLE 10-continued

| Comparative Example 1 (P&G SensiStop ™) Formulation: Strip | Comparative Example 2 (Product name: Parodontax ™) Formulation: Toothpaste | Comparative Example 3 (Alginate Gel) Formulation: Gel | Comparative Example 5 Dental impression material (Selection VPS Putty) Reactive silicone gel (Formulation: First formulation, Second formulation) |
|---|---|---|---|
| Sodium Benzoate Potassium Sorbate PE film | | | |

Comparative Example 1 used P&G SensiStop (containing active ingredient of improving sensitive teeth) and Comparative Example 2 used Parodontax (containing active ingredient of improving gingivitis). Comparative Example 3 used PVA Gel prescription (Water-soluble gel prescription, improving gingivitis/periodontitis) and Comparative Example 5 used dental impression material prescription (silicone dual-syringe prescription).

[Tests for Comparing Viscosity, Solubility and Convenience of Use Before Attachment or at the Beginning of Attachment and Just Before Removal]

Test Method

1. Hardness comparison test (Test method: measured by using Texture Analyzer)

Evaluation device: Stable Micro System TA XT Plus

Evaluation method: Hardness of Comparative Example and Example was measured by using Texture Analyzer.

Hardness was measured at compression test mode of TA (Texture Analyzer). After filling Example and Comparative Example into a 50 mL beaker, a 20 mm diameter aluminum probe for hardness measurement was set, and then hardness was measured with test speed of 1.5 mm/s, distance as target mode and distance of 10 mm. The hardness calculated from the device is the peak value of the first cycle.

① Hardness at the time of manufacture: In the case of prescription consisting of the first formulation and the second formulation, each hardness measured before mixing the first formulation and the second formulation. In the case of consisting of only the first formulation, the hardness at the time of manufacture was referred to the same as the hardness before the first application.

② Hardness at the first application: In the case of prescription consisting of the first formulation and the second formulation, hardness right after mixing. In the case of consisting of only the first formulation, the hardness was referred to the same as the hardness at the time of manufacture.

③ Hardness in adhesion: In the case of consisting of the first formulation and the second formulation, hardness is increased from the moment of mixing, and the hardness means the hardness in the state where shape transformation can occur even at a small pressure (Hardness when adhered to the desired site)

④ Hardness just before removal or upon completion of drug release: Hardness when no further hardness increase occurs. Hardness just before removal. Hardness when drug release is completed.

For example, in the case of a prescription for treating and preventing gingivitis, which consists of the first formulation and the second formulation, and is attached for 30 min, ① Hardness at the time of manufacture means each hardness before mixing, ② Hardness at the first application means the hardness just before application to teeth (when consisting of the first formulation and the second formulation, it means the hardness right after mixing) ③ Hardness in adhesion means the hardness at 10 min after application to teeth, ④ Hardness just before removal or upon completion of drug release means the hardness at 30 min after application to teeth.

2. Compressibility comparison test (Test method: measured by using Texture Analyzer)

Evaluation device: Stable Micro System TA XT Plus

Evaluation method: compressibility of Comparative Example and Example was measured by using Texture Analyzer.

Compressibility was measured at compression test mode of TA (Texture Analyzer). After filling Example and Comparative Example into a 50 mL beaker, a 20 mm diameter aluminum probe for compressibility measurement was set, and then compressibility was measured with test speed of 1.5 mm/s, distance as target mode and distance of 10 mm. The compressibility calculated from the device is the area value of the first cycle.

3. Malleability comparison test (Test method: Degree of stretch when pressing with a constant force after measuring the initial length)

In the case of a sample transformable on a PET film, 1 g each of the sample was made to have the same length and breadth (1 cm$^2$), a PE film was placed thereon, and then a 1 cm$^2$ grid plate was to show the PE film below. Then, when pressing the sample with a constant force (2 kgf/cm$^2$), the degree of stretch in length was measured using a 1 cm$^2$ grid plate, and elongation percentage was calculated by calculating the average degree of elongation in all directions. The elongation percentage was measured under a general laboratory condition, i.e., under a condition of relative humidity of about 65%, 25° C.

4. Drug release rate comparison test (Test method: after releasing test, the concentration of an active ingredient in a solution was quantified)

A) Manipulation 0.9% Sodium chloride solution 500 mL is poured in a test tube and a temperature of a test solution is maintained at 32±0.5° C. during drug release test. Example or Comparative Example as a sample is fixed on the upper side of a disk which can be used as a sinker without absorbing, interfering or reacting so that a target attachment surface faces outward. Then, the disk is placed in the test tube with the sample-attached side facing up, and drug release time is calculated from this point of time. The sample-attached disk is aligned parallel to the bottom of the test tube and a paddle blade. Distance between the paddle blade and the sample surface is set to 25±2 mm, and revolutions per min (rpm) is set to 25. At the time of sampling, 100 mL of sample solution is collected at a fixed position (a position 1 cm away from the wall of the test tube, between the top of the paddle blade and the test liquid surface) 30 min after the start of the test.

B) Drug Analysis Method

Depending on the drug or the content, an appropriate analysis is selected. For example, peroxides are analyzed by titration, metal salts are analyzed by ICP analysis, and natural extracts are analyzed by HPLC.

5. Convenience of use comparison test (Adhesive force, shape retention force, adhesive force, removability and the like)

The characteristics of the formulation applied to the target in the oral cavity cause the inconvenience to use because the formulation is smeared to the hands while being applied. Further, those cause the inconvenience to use because the formulation is smeared to gums or hands while applying and standing for a certain time and is smeared to the hand during removal. Wet type is characterized in that it is smeared to the hands when touched, and dry type is characterized in that it is not smeared when touched by hands because it maintains its shape.

[Efficacy/Effect Comparison Test]

1. Clinical survey related to improvement of sensitive teeth for humans

1) Test subject and instructions: Example 2 group and Comparative Example 1 group were attached to the sensitive teeth area for 10 min once a day and then removed.

2) After 1 week use, the survey was conducted to 15 volunteers who felt sensitive teeth per each group using 3-point Likert scale.

3) Criteria 1 point: Compared to before use, the sensitive teeth symptoms were similar or worsened.

2 point: Compared to before use, the sensitive teeth symptoms were slightly relieved.

3 point: Compared to before use, the sensitive teeth symptoms were a lot relieved.

2. Clinical survey related to improvement of gingivitis symptoms-relief of gum pain for humans 1) Test subject and instructions: Examples 1 and groups and Comparative Example 2 group were attached to the gum pain area for 10 min once a day and then removed.

2) After 1 week use, the survey was conducted to 15 volunteers who felt gum pain per each group using 3-point Likert scale.

3) Criteria 1 point: Compared to before use, the gum pain symptoms were similar or worsened.

2 point: Compared to before use, the gum pain symptoms were slightly relieved.

3 point: Compared to before use, the gum pain symptoms were a lot relieved.

3. Evaluation of whitening effect by in vitro tooth whitening evaluation method using artificial teeth (1) Preparation and Coloring of Hydroxyapatite (HAP) Tablet Sample Artificial teeth were made by using hydroxyapatite, a component that forms 96% or more of teeth. Namely, hydroxyapatite powder was tableted with IR press or tablet machine and then sintered at 1000° C. According to Stookey method, a process of impregnating a sample in TSB (trypticase soybroth) solution in which tea, coffee, iron and mucin protein were dissolved and drying thereof was repeated for 1 week to prepare a colored artificial sample. The colored sample was washed lightly with running water using a toothbrush to remove stains that could be easily dissolved or easily removed by water, and then dried. The initial L (lightness) value was measured with a chroma meter.

(2) In Vitro Tooth Whitening Evaluation Method Using Colored Artificial Teeth

After attaching Example 4 and Comparative Example 3 to a colored artificial teeth, respectively, the artificial teeth was allowed to stand for 30 min under conditions of the oral cavity, i.e., 37° C., 98% humidity. The sample was washed with water after removing Example 4 and Comparative Example 3 and then dried. Then, L value was measured. The delta L value, which is the difference between the L values before and after attachment, was calculated.

[Test for Comparing Hardness Before Attachment or at the Beginning of Attachment and Just Before Removal]

1. Hardness of Example and Comparative Example at each stage

TABLE 11

| | Example 4 | Example 1 | Example 2 | Comparative Example 3 | Comparative Example 5 |
|---|---|---|---|---|---|
| At the time of manufacture | Not measurable | Not measurable | Not measurable | Not measurable | First formulation 100 g Second formulation 100 g |
| First application | 150 g | 180 g | 120 g | Not measurable | 300 g |
| In adhesion | 150 g | 5580 g | 450 g | Not measurable | >33,600 g |
| Just before removal (Upon completion of drug release) | 150 g | 12,000 g | 600 g | Not measurable | >>Not measurable |

As listed in Table 11, the oral preparations of Examples of the present invention had the hardness in adhesion of around 5,000 g or less, and those have advantages that it can be transformed by a small force due to low hardness, and therefore, when pressed lightly with a finger at the beginning, it can be stretched to the desired length, and the preparation has little feeling of foreign body in gums or oral cavity because the preparation is soft. On the contrary, in the case of Comparative Example 3, there is no hardness, so it is equivalent to Examples in terms of softness. However, it has disadvantages that it is difficult to maintain shape after application because it is a general liquid gel, it is scattered by pressing with a finger, it is inconvenient to use because it is smeared to the hands and easily smeared to the contact site to the gums, and it is easily washed out in the humid oral cavity. In the case of Comparative Example 5, there is high hardness. Thus, it has disadvantages that it may give a burden to soft gums because it is impossible to transform shape if it is not quickly adhered after application due to its hardness, and it is impossible to release a drug after the hardness is increased.

2. Compressibility of Example and Comparative Example at each stage

TABLE 12

|  | Example 4 | Example 1 | Example 2 | Comparative Example 3 | Comparative Example 5 |
|---|---|---|---|---|---|
| At the time of manufacture | Not measurable | Not measurable | Not measurable | Not measurable | First formulation 100 gs Second formulation 100 gs |
| First application | 700 gs | 680 gs | 650 gs | Not measurable | 1200 gs |
| In adhesion | 700 gs | 11,000 gs | 1500 gs | Not measurable | >55,000 gs |
| Just before removal (Upon completion of drug release) | 700 gs | 16,000 gs | 2000 gs | Not measurable | >>Not measurable |

As listed in Table 12, the oral preparations of Examples of the present invention have low compressibility in adhesion, and it means that those do not take much effort to make the desired transformation for a certain period of time. Those have an advantage that when pressed lightly with a finger, desired deformations can be obtained, including not only size deformation but also shape deformation, which makes it possible to easily fill teeth gaps in many teeth simultaneously even if the teeth are uneven. On the contrary, in the case of Comparative Example 3, it has disadvantages that it is difficult to maintain shape after application because it is a general liquid gel without hardness, it is scattered by pressing with a finger, it is inconvenient to use because it is smeared to the hands and easily smeared to the contact site to the gums, and it is easily washed out in the humid oral cavity. In the case of Comparative Example 5, compressibility is sharply increased within several min after application and the value is too high. Thus, it has disadvantages that it is hard to use because it is impossible to transform shape if it is not quickly adhered after application due to its hardness, and it is difficult to release a drug.

3. Comparison of malleability of Example and Comparative Example

TABLE 13

|  | Example 4 | Example 1 | Comparative Example 3 | Comparative Example 5 |
|---|---|---|---|---|
| At first application (Within 2 min) | >300% | >150% | Not maintained shape | 150% |
| In adhesion (Within 10 min) | >300% | >150% | Not maintained shape | Fixed |
| Just before removal | >300% | 150% | Not maintained shape | Fixed |

TABLE 13-continued

|  | Example 4 | Example 1 | Comparative Example 3 | Comparative Example 5 |
|---|---|---|---|---|
| (after 30 min) |  |  |  |  |

As can be seen from Table 13, the preparations of the present invention could maintain the malleability just before removal. By such malleability, the preparations of the present invention could be completely adhered to gap between teeth, and effectively deliver the drug to gaps between teeth and gums.

4. Drug release rate of Example and Comparative Example

TABLE 14

|  | Example 1 | Example 2 | Comparative Example 3 |
|---|---|---|---|
| After 10 min from attachment | 50% | 60% | 5% |
| After 30 min from attachment | >70% | >80% | <5% |

As can be seen from Table 14, in the case of Examples, it can be confirmed that 70% or more of the drug was released at the time of removal of the preparation, which was 30 min after attachment, based on the loaded amount of the drug. However, in the case of Comparative Example, it can be confirmed that removal of the preparation increased the hardness and limited the drug release.

5. Comparison of convenience of use of Example and Comparative Example

TABLE 15

|  | Example 4 | Example 1 | Comparative Example 1 | Comparative Example 2 | Comparative Example 3 |
|---|---|---|---|---|---|
| Degree of smear at the time of manufacture | First formulation (Smeared: Wet type) Second formulation (Smeared: Wet type) | First formulation (Smeared: Powder type) Second formulation (Smeared: Wet type) | Smeared (Wet type) | Smeared (Wet type) | Smeared (Wet type) |
| Degree of smear at first application | Not smeared (Dry type) | Almost not smeared (Like dry type) | Smeared (Wet type) | Smeared (Wet type) | Smeared (Wet type) |
| Degree of smear just before removal | Not smeared (Dry type) | Not smeared | Smeared (Wet type) | Smeared (Wet type) | Smeared (Wet type) |

As cab be seen from Table 15, in the case of Comparative Examples of the present invention, the drug was smeared to the hands in the course of applying the preparations on the surface of teeth, but Examples of the present invention could be conveniently used because the drug was almost not smeared to the hands.

TABLE 16

|  | Example 4 | Example 1 | Comparative Example 1 | Comparative Example 2 |
|---|---|---|---|---|
| Survey score for sensitive teeth | — | 2.7 | 1.5 | — |
| Survey score for gum pain | 2.4 | — | — | 1.4 |

As can be seen from Table 16, it was confirmed that Example 1 had better effect of relieving sensitive teeth, compared to Comparative Example 1, and it was confirmed that Example 4 had better effect of relieving gum pain symptoms, compared to Comparative Example 2.

These results suggest that the formulations of Examples of the present invention have excellent degree of adhesion to teeth and gaps between teeth, so that active ingredients are effectively delivered to the target site.

Further, because Comparative Examples 1 and 2 are toothpaste-type and the holding time of the drug delivered at the time of the first application (brushing) was not long, the active ingredient gradually disappeared over time. However, in the case of the preparation of Examples of the present invention providing the time for stable penetration of the active ingredient for a certain period of time, it was thought that loss rate of the active ingredient was low.

TABLE 17

|  | ΔL (Use once) | ΔL (Use twice) |
|---|---|---|
| Example 2 | 16.54 ± 2.19 | 31.49 ± 3.05 |
| Comparative Example 3 | 5.29 ± 1.54 | 9.89 ± 1.85 |

As can be seen from Table 17, Example 2 showed better tooth whitening effect, compared to Comparative Example 3. It was confirmed that in the case of Comparative Example 3, which is gel-type, the amount of the active ingredient delivered to teeth was smaller than the loaded amount, and the whitening effect was significantly low because the amount that flows down or disappears by force without being fixed after being applied to teeth was a lot.

INDUSTRIAL APPLICABILITY

The preparation of the present invention can be well adhered to gaps between teeth well, and therefore, it can effectively deliver a drug to teeth of gaps between teeth. The present invention can provide a preparation attachable in the oral cavity, which is convenient to use because it does not flow down when applied to teeth.

The present invention has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

The invention claimed is:

1. A preparation for attaching to teeth or tooth peripheries, comprising:
    an oral composition in a hardening ointment-phase; and
    an active ingredient for intra-oral delivery,
    wherein the preparation becomes hardened and substantially loses its moldability in 5 minutes to 3 hours after the preparation is attached to teeth or tooth peripheries under humidity and temperature conditions of the oral cavity, and
    wherein the oral composition in the hardening ointment-phase comprises a phase transition material, a phase transition auxiliary material, an attachment-enhancing material of a phase transition composition, and a material for helping drug release,
    wherein the preparation is two-formulation preparation consisting of a first formulation and a second formulation,
    wherein one of the first formulation or the second formulation contains an acid and the other of the first formulation or the second formulation contains a base,
    wherein the phase transition material includes carrageenan, pectin, xyloglucan, gellan gum, ammonium alginate, magnesium alginate, potassium alginate, sodium alginate, lithium alginate, chitosan, poly-lactic acid (poly(D,L-lactic acid)), polylactide-co-glycolide (poly(DL-lactide-co-glycolide)), poly-caprolactone, polyacrylic acid (carbopol), polyvinylacetal diethyl aminoacetate (AEA), hydroxypropylmethyl cellulose, poly(methacrylic acid)-poly(ethylene glycol), poly(D,L-lactide)-block-poly(ethylene glycol)-block-poly(D,L-lactide), PEG-oligoglycolyl-acrylate, poly(N-isopropyl acrylamide), sucrose acetate isobutyrate, polyvinyl alcohol, glyceryl monooleate, glyceryl monolinoleate, glyceryl monoarachidonate, glyceryl monostearate, or a mixture thereof,
    wherein the phase transition auxiliary material includes a calcium ion source of calcium carbonate, calcium phosphate dibasic ($CaHPO_4$), barium carbonate, zinc carbonate, calcium chloride, calcium lactate, calcium citrate, calcium aspartate, calcium saccharate, calcium oxovalerate, calcium gluconate, calcium lactobionate or calcium lactogluconate; a chelating agent of barium carbonate, zinc carbonate, sodium bicarbonate, sodium carbonate, tetraborate or tripolyphosphate; acetic acid, malic acid, lactic acid, gluconic acid, ascorbic acid or a mixture or a salt thereof; or NaOH, KOH or a mixture thereof, and
    wherein the attachment-enhancing material of the phase transition composition includes precipitated silica for thickening, colloidal silicone dioxide, polyvinyl pyrrolidone, poly methyl vinyl ether and maleic acid copolymer, shellac, rosin, poloxamer, hyaluronic acid, acrylate copolymer, hydroxypropyl methyl cellulose (HPMC), hydroxypropyl cellulose (HPC), polyacrylic acid, polyethylene glycol, ethyl cellulose or a mixture thereof, or a crosslinked body thereof.

2. The preparation of claim 1, wherein the active ingredient is mixed with the oral composition in the hardening ointment-phase.

3. The preparation of claim 1, wherein the preparation becomes hardened and substantially loses its moldability in 10 minutes to 3 hours after the preparation is attached to teeth or tooth peripheries under the humidity and temperature conditions of the oral cavity.

4. The preparation of claim 1, wherein the becoming hardened and losing its moldability means that the preparation becomes to have a viscosity of 5000 cps or higher, which is measured by using Brookfield viscometer equipped with No. 6, 7 spindles at 20° C., 5 to 20 rpm, in 5 minutes to 3 hours after the preparation is attached to teeth or tooth peripheries.

5. The preparation of claim 1, wherein a viscosity measured at the time after 5 minutes to 3 hours from the attachment of the preparation to teeth or tooth peripheries is increased two times or more, compared to the viscosity measured at the time of the attachment of the preparation to teeth or tooth peripheries.

6. A preparation for attaching to teeth or tooth peripheries, comprising: a malleable oral composition; and an active ingredient for intra-oral delivery,
   wherein the preparation becomes hardened and substantially loses its moldability in 5 minutes to 3 hours after the preparation is attached to teeth or tooth peripheries under humidity and temperature conditions of the oral cavity, and
   wherein the malleable oral composition comprises a phase transition material, a phase transition auxiliary material, an attachment-enhancing material of a phase transition composition, and a material for helping drug release,
   wherein the preparation is two-formulation preparation consisting of a first formulation and a second formulation,
   wherein one of the first formulation or the second formulation contains an acid and the other of the first formulation or the second formulation contains a base,
   wherein the phase transition material includes carrageenan, pectin, xyloglucan, gellan gum, ammonium alginate, magnesium alginate, potassium alginate, sodium alginate, lithium alginate, chitosan, poly-lactic acid (poly(D,L-lactic acid)), polylactide-co-glycolide (poly(DL-lactide-co-glycolide)), poly-caprolactone, polyacrylic acid (carbopol), polyvinylacetal diethyl aminoacetate (AEA), hydroxypropylmethyl cellulose, poly(methacrylic acid)-poly(ethylene glycol), poly(D,L-lactide)-block-poly(ethylene glycol)-block-poly(D,L-lactide), PEG-oligoglycolyl-acrylate, poly(N-isopropyl acrylamide), sucrose acetate isobutyrate, polyvinyl alcohol, glyceryl monooleate, glyceryl monolinoleate, glyceryl monoarachidonate, glyceryl monostearate, or a mixture thereof,
   wherein the phase transition auxiliary material includes a calcium ion source of calcium carbonate, calcium phosphate dibasic (CaHPO$_4$), barium carbonate, zinc carbonate, calcium chloride, calcium lactate, calcium citrate, calcium aspartate, calcium saccharate, calcium oxovalerate, calcium gluconate, calcium lactobionate or calcium lactogluconate; a chelating agent of barium carbonate, zinc carbonate, sodium bicarbonate, sodium carbonate, tetraborate or tripolyphosphate; acetic acid, malic acid, lactic acid, gluconic acid, ascorbic acid or a mixture or a salt thereof; or NaOH, KOH or a mixture thereof, and
   wherein the attachment-enhancing material of the phase transition composition includes precipitated silica for thickening, colloidal silicone dioxide, polyvinyl pyrrolidone, poly methyl vinyl ether and maleic acid copolymer, shellac, rosin, poloxamer, hyaluronic acid, acrylate copolymer, hydroxypropyl methyl cellulose (HPMC), hydroxypropyl cellulose (HPC), polyacrylic acid, polyethylene glycol, ethyl cellulose or a mixture thereof, or a crosslinked body thereof.

7. The preparation of claim 6, wherein the active ingredient is mixed with the malleable oral composition and dispersed in the preparation.

8. The preparation of claim 6, wherein the preparation has an initial hardness of from 0.1 g to 20,000 g, measured at Compression mode of Texture Analyzer (TA), at the time of attachment.

9. The preparation of claim 6, wherein the preparation has a final hardness of 40,000 g or less, measured at Compression mode of Texture Analyzer (TA), at the time of removal.

10. The preparation of claim 9, wherein the time of removal is when an amount of the active ingredient released into the oral cavity is 60 wt % or more, based on an amount of the active ingredient contained in the initial preparation, after 30 minutes from the attachment of the preparation to teeth or tooth peripheries.

11. The preparation of claim 6, wherein the preparation has an initial compressibility of 0.1 to 30,000 gs, measured at Compression mode of Texture Analyzer (TA).

12. The preparation of claim 6, wherein the preparation has a final compressibility of 50,000 gs or less, measured at Compression mode of Texture Analyzer (TA).

13. The preparation of claim 6, wherein the preparation increases its area when the preparation is pressed by applying force at beginning of attachment.

14. The preparation of claim 1, wherein the active ingredient is sodium fluoride, stannous fluoride, indium fluoride, amine fluoride, sodium monofluorophosphate, tetrasodium pyrophosphate (TSPP), sodium acid pyrophosphate (SAPP), sodium tripolyphosphate (STP), sodium potassium pyrophosphate, tetrapotassium pyrophosphate, acidic sodium metaphosphate, acidic sodium polyphosphate, triclosan, chlorhexidine, alexidine, hexetidine, sanguinarine, benzalkonium chloride, salicylanilide, domiphen bromide, cetylpyridinium chloride (CPC), tetradecylpyridinium chloride (TPC), aspirin, ketorolac, flurbiprofen, piroxicam, meclofenamic acid, thiamine, riboflavin, nicotinic acid, pantothenic acid, pyridoxine, biotin, folic acid, vitamin B12, lipoic acid, ascorbic acid, vitamin A, vitamin D, vitamin E, vitamin K, titrated extract of *Zea Mays* L. unsaponifiable fraction, Magnoliae Cortex, Myrrha, Rhatany, Chamomile, policresulen, titrated extract of Centella Asiatica, nutmeg extract, dexpanthenol, β-sitosterol, acetyl salicylic acid, zinc chloride, potassium phosphate, potassium diphosphate, calcium chloride, oxalic acid, potassium oxalate, ferric oxalate, vitamin E, or a mixture thereof.

15. The preparation of claim 1, wherein the first formulation and the second formulation of the two-formulation preparation are configured to be mixed and then applied to teeth or tooth peripheries, and
   viscosity of a mixture of the first formulation and the second formulation measured after mixing the two formulations for application to teeth or tooth peripheries is increased, compared to before mixing, wherein the preparation hardens by losing moldability.

16. The preparation of claim 1, wherein the two-formulation preparation contains the active ingredient in the first formulation, in the second formulation, or in the both first and second formulations.

17. The preparation of claim 1, wherein water-solubility of the preparation, measured at 32° C., 1 atm after 5 minutes to 3 hours from attachment of the preparation to teeth or tooth peripheries, is 20 wt % or less.

18. The preparation of claim 1, wherein the preparation further comprises a backing layer.

19. A preparation for attaching to teeth or tooth peripheries, comprising:

an oral composition, which has malleability, and is in an ointment form before being attached to teeth or tooth peripheries and then hardens after attachment; and an active ingredient for intra-oral delivery, wherein the preparation becomes hardened and substantially loses its moldability in 5 minutes to 3 hours after the preparation is attached to teeth or tooth peripheries under humidity and temperature conditions of the oral cavity, and wherein the oral composition in the hardening ointment-phase comprises a phase transition material, a phase transition auxiliary material, an attachment-enhancing material of a phase transition composition, and a material for helping drug release, wherein the preparation is two-formulation preparation consisting of a first formulation and a second formulation, wherein one of the first formulation or the second formulation contains an acid and the other of the first formulation or the second formulation contains a base, wherein the phase transition material includes carrageenan, pectin, xyloglucan, gellan gum, ammonium alginate, magnesium alginate, potassium alginate, sodium alginate, lithium alginate, chitosan, poly-lactic acid (poly(D,L-lactic acid)), polylactide-co-glycolide (poly(DL-lactide-co-glycolide)), poly-caprolactone, polyacrylic acid (carbopol), polyvinylacetal diethyl aminoacetate (AEA), hydroxypropylmethyl cellulose, poly(methacrylic acid)-poly(ethylene glycol), poly(D,L-lactide)-block-poly(ethylene glycol)-block-poly(D,L-lactide), PEG-oligoglycolyl-acrylate, poly(N-isopropyl acrylamide), sucrose acetate isobutyrate, polyvinyl alcohol, glyceryl monooleate, glyceryl monolinoleate, glyceryl monoarachidonate, glyceryl monostearate, or a mixture thereof, wherein the phase transition auxiliary material includes a calcium ion source of calcium carbonate, calcium phosphate dibasic ($CaHPO_4$), barium carbonate, zinc carbonate, calcium chloride, calcium lactate, calcium citrate, calcium aspartate, calcium saccharate, calcium oxovalerate, calcium gluconate, calcium lactobionate or calcium lactogluconate; a chelating agent of barium carbonate, zinc carbonate, sodium bicarbonate, sodium carbonate, tetraborate or tripolyphosphate; acetic acid, malic acid, lactic acid, gluconic acid, ascorbic acid or a mixture or a salt thereof; or NaOH, KOH or a mixture thereof, and wherein the attachment-enhancing material of the phase transition composition includes precipitated silica for thickening, colloidal silicone dioxide, polyvinyl pyrrolidone, poly methyl vinyl ether and maleic acid copolymer, shellac, rosin, poloxamer, hyaluronic acid, acrylate copolymer, hydroxypropyl methyl cellulose (HPMC), hydroxypropyl cellulose (HPC), polyacrylic acid, polyethylene glycol, ethyl cellulose or a mixture thereof, or a crosslinked body thereof.

20. The preparation of claim 19, wherein the preparation further comprises a backing layer.

* * * * *